United States Patent [19]

Lavagnino et al.

[11] 4,207,343
[45] Jun. 10, 1980

[54] 1-PHENYL-3-(SUBSTITUTED PHENOXY)PROPYLAMINES

[75] Inventors: Edward R. Lavagnino; Lawrence J. McShane; both of Indianapolis, Bryan B. Molloy, North Salem, all of Ind.

[73] Assignee: Eli Lilly and Company, Indianapolis, Ind.

[21] Appl. No.: 917,819

[22] Filed: Jun. 22, 1978

[51] Int. Cl.² .......................... A01N 9/20; A01N 9/24; C07C 93/06
[52] U.S. Cl. .................................. 424/330; 260/349; 260/453 AR; 260/501.18; 260/501.19; 260/546; 260/549; 260/570.5 R; 260/570.6; 260/651 R; 260/651 HA; 424/316; 560/61; 560/62; 562/471; 562/472; 568/631
[58] Field of Search ......... 260/570.5 R, 570.6, 570.7, 260/501.10; 424/330, 316

[56] References Cited

U.S. PATENT DOCUMENTS

| 3,106,564 | 10/1963 | Fleming et al. | 260/570.5 X |
| 3,562,330 | 2/1971 | Nordin | 260/570.5 |
| 4,018,895 | 4/1977 | Molloy et al. | 260/570.6 |

OTHER PUBLICATIONS

La Forge, "Journal American Chemical Society", vol. 50, pp. 2471–2477 (1928).

*Primary Examiner*—Robert V. Hines
*Attorney, Agent, or Firm*—James L. Rowe; Arthur R. Whale

[57] ABSTRACT

1-Phenyl-3-(optionally substituted phenoxy)-propylamines, inhibitors of norepinephrine uptake.

4 Claims, No Drawings

1-PHENYL-3-(SUBSTITUTED PHENOXY)PROPYLAMINES

BACKGROUND OF THE INVENTION

3-Phenyl-3-(optionally substituted phenoxy)propylamines are disclosed in U.S. Pat. No. 4,018,895. These compounds block the uptake of various physiologically active monoamines including serotonin, norepinephrine and dopamine. This utility is characteristic of antidepressant psychotropic agents.

SUMMARY OF THE INVENTION

This invention provides 1-phenyl-3-(optionally substituted phenoxy)propylamines of the formula:

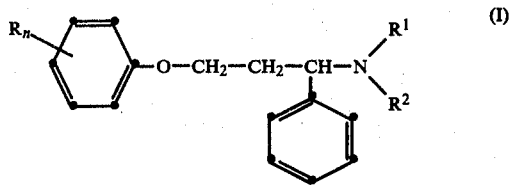

wherein R is $CF_3$, $OCH_3$ or $CH_3$, $R^1$ and $R^2$, taken singly, are H or $CH_3$, and n is 0 or 1; and non-toxic pharmaceutically acceptable acid addition salts thereof.

The above formula comprehends the N,N-dimethyl, N-methyl derivatives of 1-phenyl-3-(trifluoromethylphenoxy or anisyloxy or tolyloxy or phenoxy)propylamine as well as the primary amines themselves. Ortho, meta and para substitution is included for each of the substituted phenoxy groups represented by R.

Pharmaceutically-acceptable salts of the amine bases represented by the above formula are formed by reaction with suitable acids. Included within the scope of this invention are salts derived from inorganic acids such as: hydrochloric acid, nitric acid, phosphoric acid, sulfuric acid, hydrobromic acid, hydriodic acid, nitrous acid, phosphorous acid and the like; as well as salts derived from organic acids including aliphatic mono and dicarboxylates, phenyl-substituted alkanoates, hydroxy alkanoates and alkanedioates, aromatic acids, aliphatic and aromatic sulfonic acids etc. Such pharmaceutically-acceptable salts thus include: sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, benzenesulfonates, toluenesulfonate, chlorobenzenesulfonate, xylenesulfonate, phenylacetate, phenylpropionate, phenylbutyrate, citrate, lactate, β-hydroxybutyrate, glycollate, maleate, tartrate, methanesulfonate, propanesulfonates, naphthalene1-sulfonate, naphthalene-2-sulfonate, mandelate and the like salts.

Compounds illustrative of the scope of this invention include:
1-phenyl-3-(m-trifluoromethylphenoxy)propylamine phosphate
N-methyl 1-phenyl-3-(p-trifluoromethylphenoxy)propylamine benzoate
N,N-dimethyl 1-phenyl-3-(o-trifluoromethylphenoxy)-propylamine tartrate
N-methyl 1-phenyl-3-(o-tolyloxy)propylamine sulfate
N,N-dimethyl 1-phenyl-3-(p-tolyloxy)propylamine bisulfate
N-methyl 1-phenyl-3-(m-tolyloxy)propylamine dihydrogen phosphate
N,N-dimethyl 1-phenyl-3-(phenoxy)propylamine maleate
N,N-dimethyl 1-phenyl-3-(p-anisyloxy)propylamine oxalate
N-methyl 1-phenyl-3-(m-anisyloxy)propylamine p-tosylate
N,N-dimethyl 1-phenyl-3-(m-anisyloxy)propylamine mesylate and the like.

The compounds of this invention can be prepared by several alternate routes. One of these synthetic procedures begins with the reaction of ω-bromopropylbenzene and a phenol of the formula:

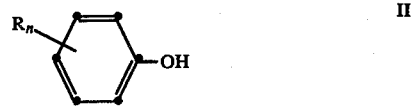

(wherein R and n have the same meaning as before) in an inert solvent in the presence of base to yield a 1-phenyl-3-phenoxy (or substituted phenoxy) propane. Bromination of this propane derivative with N-bromosuccinimide in the presence of light or a reaction promoter such as benzoyl peroxide (thus utilizing a free radical mechanism) yields a 1-bromo-1-phenyl-3-phenoxy (or substituted phenoxy) propane. The free radical bromination occurs preferentially on the carbon ω to the phenyl group rather than on one of the other carbons of the alkyl chain.

This 1-bromo-1-phenyl-3-phenoxy propane can then be reacted with dimethylamine, monomethylamine or ammonia, using a sealed reaction vessel in all instances, to yield compounds of this invention according to Formula I above.

The 1-phenyl-3-phenoxy (or substituted phenoxy) propane can be prepared by an alternate route involving the reaction of a 3-chloro-1-bromo-1-phenylpropane with phenol in the presence of base. This reaction yields predominantly the 1-phenyl-1-phenoxy propyl chloride but a side-product of the reaction is a 1-phenyl-3-phenoxy (or substituted phenoxy)1-propene. The reaction producing this unsaturated derivative is set forth in *Bull. Soc. Chim. Fr.* 1972, 1540-4, page 1542 left hand column. Hydrogenation of this propene yields the desired 1-phenyl-3-phenoxy (or substituted phenoxy) propane.

An alternate route which can be employed to prepare chiefly the primary amine compounds of this invention involves the reaction of the same phenol (II) with 1,2-dibromoethane (ethylenedibromide) in the presence of base to yield a β-bromoethylphenyl (or substituted phenyl)ether. The reaction of this bromo compound with the sodium salt of 2-phenylmalonic ester yields a 2-phenyl-2-[β-(phenoxy or substituted phenoxy)ethyl]malonic ester. Saponification of the dibasic malonic ester produces a dibasic acid, decarboxylation of which gives a 2-phenyl-4-phenoxy (or substituted phenoxy)-n-butyric acid. The mixed anhydride of this acid formed with ethyl chloroformate is prepared using triethylamine or other tertiary bases as a acid scavenger. The mixed anhydride is then reacted with sodium azide (NaN$_3$) to yield the corresponding carboxylic acid azide. Subjecting this carboxazide to Curtius rearrangement conditions yields a 1-phenyl-3-(phenoxy or substituted phenoxy)propylisocyanate, which compound, upon treatment with concentrated hydrochloric acid, yields the corresponding primary amine. These primary amines come within the scope of Formula I above.

The corresponding dimethylamino compound can be prepared from the primary amine by methylation using formaldehyde and formic acid or by other standard procedure. The monomethylamine can in turn be prepared from the dimethylamine by the reaction of the tertiary dimethylamine group with cyanogen bromide or ethyl chloroformate followed by hydrolysis to yield the corresponding secondary amine.

This invention is further illustrated by the following specific examples:

EXAMPLE 1

Preparation of 1-Phenyl-3-(m-anisyloxy)propylamine

A solution was prepared from 124 g. of m-methoxyphenol and 1 L. of methanol. 65 g. of 85% aqueous potassium hydroxide were added thereto with stirring, thus forming the potassium salt of the phenol. The reaction mixture was stirred at room temperature for 30 minutes after which time 261 ml. of 1,2-dibromoethane were added. This new reaction mixture was heated at reflux temperature for about 40 hours, after which time the volatile constituents were removed by evaporation. The resulting residue was dissolved in chloroform and the chloroform solution washed first with water, secondly three times with 5 N aqueous sodium hydroxide, next twice more with water and finally with saturated aqueous sodium chloride. The chloroform layer was separated and dried and the chloroform removed by evaporation in vacuo. The residue was a yellowish oil weighing 75 g. comprising m-anisyl β-bromoethyl ether distilling in the range 125°–127° C. at 1 torr. Product distilling in this range was redistilled and had the following elemental analysis:

Analysis calc.: C, 46.78; H, 4.80; Br, 34.58. Found: C, 46.99; H, 4.89; Br, 34.70.

Twenty grams of 50% sodium hydride in the form of a suspension in mineral oil were placed in a 1 liter three-neck round-bottom flask under a nitrogen atmosphere. The sodium hydride suspension was washed three times with hexane and the hexane washes were discarded. 250 ml. of dimethylformamide (DMF) were added followed by 96.5 g. of diethyl 2-phenylmalonate in 150 ml. of benzene. This mixture was allowed to stir at room temperature for about 1 ½ hours during which time the sodium salt of diethyl 2-phenylmalonate formed. Next, 87 g. of m-anisyl β-bromoethyl ether in 100 ml. of benzene were added. The reaction mixture was heated to reflux for 3½ hours and then allowed to stir overnight at ambient temperature. The reaction mixture was then diluted with 500 ml. of water and the resulting aqueous mixture extracted three times with ether. The ether extracts were separated and combined. The combined extracts were washed twice with water, once with saturated aqueous sodium chloride and were then dried. Evaporation of the ether yielded 144 g. of a pale yellowish oil comprising diethyl 2-phenyl-2-[β-(m-anisyloxy)ethyl]-malonate formed in the above reaction. Volatile impurities were removed by distillation at 0.05 torr. up to 150° C. The resulting residue weighed 90 g. Physical characteristics indicated that a compound of the postulated structure had been obtained.

90 g. of the diester formed above were placed in a 3 L. round-bottom flask to which 1.5 L. of 80% aqueous ethanol were added with stirring. Next, 54 g. of 85% solid potassium hydroxide were added and the resulting mixture heated under reflux for about 4 hours and then overnight at ambient temperature. The reaction mixture was transferred to a round-bottom flask and the ethanol removed by evaporation in vacuo. The reaction mixture was then diluted with water and the aqueous mixture extracted with 300 ml. of ether. The ether extract was discarded. The aqueous layer was made acidic with 12 N aqueous hydrochloric acid while being cooled. The acidic layer was extracted three times with 500 ml. portions of ether. The ether extracts were combined and the combined extracts washed twice with water, once with saturated aqueous sodium chloride and were then dried. Evaporation of the ether yields 80 g. of a pale yellowish solid comprising 4-(m-anisyloxy)-2-phenylbutyric acid (formed in the above reactions including first hydrolysis of the diester and second decarboxylation of the resulting dicarboxylic acid). The acid melted at 112°–113.5° C. after recrystallization from a mixture of cyclohexane and ether.

Analysis calc.: C, 71.31; H, 6.34; O, 22.35. Found: C, 71.07; H, 6.31; O, 22.48.

About 57 g. of 4-(m-anisyloxy)-2-phenylbutyric acid were placed in a 1 L. three-neck round-bottom flask to which was added 150 ml. of acetone with stirring. The resulting solution was cooled in an ice bath. Next, 30.6 ml. of triethylamine were added. Then, while maintaining the temperature at about 0° C., 21.1 ml. of ethyl chloroformate were added in dropwise fashion at such a rate that the temperature remained in a range 0°–5° C. After the addition was completed, the reaction mixture was stirred for an additional 15 minutes after which time a solution of 26 g. of sodium azide in 75 ml. of water was added in dropwise fashion with stirring while still maintaining the temperature at about 0° C. This reaction mixture was stirred for an additional 30 minutes and was then poured into 75 ml. of a mixture of ice and water. The aqueous mixture was extracted four times with 250 ml. portions of toluene. The toluene extracts were combined and dried. The toluene solution was then transferred to a 2 L. round-bottom flask and heated on a steam bath at reflux temperature for about 2 hours. The toluene was removed by evaporation. The oily residue comprising 3-(m-anisyloxy)-1-phenylpropylisocyanate formed in the above reaction was treated with 300 ml. of 8 N aqueous hydrochloric acid and the resulting mixture stirred at room temperature for about 1 hour. The acidic mixture was then concentrated under reduced pressure during which time a gummy white precipitate formed. The acidic supernate was decanted and discarded. All volatile constituents were removed from the gummy residue by evaporation in vacuo. The dried residue, comprising 3-(m-anisyloxy)-1-phenylpropylamine hydrochloride formed in the above reaction, was recrystallized twice from an acetone-cyclohexane solvent mixture and yielded crystals melting at about 124°–126° C.; yield 12.5 g.

Analysis calc.: C, 65.41; H, 6.86; N, 4.77; Cl, 12.07. Found: C, 65.64; H, 6.61; N, 4.75; Cl, 11.90.

Following the above procedure but using p-methoxyphenol in place of m-methoxyphenol, p-anisyl β-bromoethyl ether was prepared melting at 50°–52° C. after recrystallization from a methanol-chloroform solvent mixture. The reaction of this bromoether with the sodium salt of diethyl 2-phenylmalonate followed by hydrolysis of the resulting diester and decarboxylation of the corresponding diacid yielded 4-(p-anisyloxy)-2-phenylbutyric acid melting at 114°–115° C. after recrystallization from an ethylacetate-hexane solvent mixture Analysis calc.: C, 71.33; H, 6.34; 0, 22.35. Found: C, 71.56; H, 6.09; O, 22.40.

Conversion of this acid to the azide followed by a Curtius rearrangement to produce this isocyanate followed by decomposition of the isocyanate in aqueous hydrochloric acid gave 3-(p-anisyloxy)-1-phenylpropylamine hydrochloride. The compound was a white crystalline solid after recrystallization from an ethyl acetate-methanol solvent mixture.

Analysis calc.: C, 65.41; H, 6.87; N, 4.77; Cl, 12.07. Found: C, 65.58; H, 6.77; N, 4.90; Cl, 12.03.

Following the above procedure but using p-cresol in place of m-hydroxyanisole, there was prepared p-tolyl β-bromoethyl ether boiling at 108°–110° C. at 1 torr. This bromo ether was converted via 2-phenylmalonic ester to 4-(p-tolyloxy)-2-phenylbutyric acid melting at 102°–104° C. after recrystallization from an ether-hexane solvent mixture. Still following the above procedure, the butyric acid was successively converted via the mixed anhydride with ethyl chloroformate, to the azide, then to the isocyanate via a Curtius rearrangement and then to the primary amine as the hydrochloride salt. 3-(p-Tolyloxy)-1-phenylpropylamine hydrochloride thus prepared melted at 204°–206° C. The free base was prepared by dissolving the salt in water and making the aqueous solution alkaline with 5 N aqueous sodium hydroxide. The primary amine, being insoluble in the basic solution, separated and was extracted with several 300 ml. portions of ether. The ether extracts were combined and the combined extracts washed twice with water and once with saturated aqueous sodium chloride, and were then dried. Evaporation of the ether yielded a yellowish oil comprising 3-(p-tolyloxy)-1-phenylpropylamine.

The hydrochloride salt had the following analysis:
Analysis calc.: C, 69.18; H, 7.26; N, 5.04; Cl, 12.76. Found: C, 68.91; H, 7.25; N, 5.20; Cl, 13.01.

Following the above reaction but substituting o-cresol for p-hydroxyanisole, there was obtained o-tolyl β-bromoethyl ether distilling in the range 91°–95° C. at 1 torr.

Analysis calc.: C, 50.26; H, 5.16; Br, 37.15. Found: C, 50.17; H, 5.11; Br, 37.24.

The bromoether was then transformed via diethyl 2-phenylmalonate, sodium salt to 2-phenyl-2-(β-tolyloxy)-ethyl malonic ester. Hydrolysis of the diester and decarboxylation of the resulting diacid gave 4-(o-tolyloxy)-2-phenylbutyric acid melting in the range 105°–107° C. after recrystallization from an ether-hexane solvent mixture.

Analysis calc.: C, 75.53; H, 6.71; O, 17.76. Found: C, 75.26; H, 6.50; O, 16.93.

The butyric acid was converted to the mixed anhydride with ethyl chloroformate and the anhydride to the azide by reaction with sodium azide. Curtius rearrangement of the azide yielded the corresponding isocyanate. Hydrolysis of the isocyanate in hydrochloric acid gave, ultimately, 3-(o-cresol)-1-phenylpropylamine hydrochloride melting 167.5°–169° C. after recrystallization from an ethyl acetate-methanol solvent mixture.

Analysis calc.: C, 69.18; H, 7.26; N, 5.04; Cl, 12.76. Found: C, 69.04; H, 7.43; N, 5.11; Cl, 13.00.

Following the above procedure but substituting m-cresol for m-anisole, there was prepared m-tolyl β-bromoethyl ether as a pale yellowish oil Analysis calc.: C, 50.26; H, 5.16; Br, 37.15. Found: C, 50.53; H, 5.05; Br, 37.25.

The bromoethyl ether was transformed via reaction with diethyl 2-phenylmalonate, hydrolysis of the resulting diester and decarboxylation of the resulting diacid to 4-(p-tolyloxy)-2-phenylbutyric acid melting at 133°–136° C. after recrystallization from a chloroform-cyclohexane solvent mixture.

Analysis calc.: C, 75.53; H, 6.71; O, 17.76. Found: C, 75.28; H, 6.69; O, 17.90.

The butyric acid was in turn successively transformed to the mixed anhydride with ethyl chloroformate, to the azide, to the isocyanate via a Curtius rearrangement and to the primary amine by hydrolysis. The primary amine, 3-(p-tolyloxy)-1-phenylpropylamine, was isolated as the hydrochloride salt melting at 153°–155° C. after recrystallization from an ethyl acetate-methanol-cyclohexane solvent mixture.

Analysis calc.: C, 69.18; H, 7.26; N, 5.04; Cl, 12.76. Found: C, 69.17; H, 7.25; N, 5.27; Cl, 12.71.

EXAMPLE 2

Preparation of 3-(p-Tolyloxy)-1-phenylpropylamine

Six grams of 3-(p-tolyloxy)-1-phenylpropylamine hydrochloride were added to a mixture of 200 ml. of 2 N aqueous sodium hydroxide in 500 ml. of ether. The mixture was stirred at room temperature for 1 hour after which time the ether layer containing the primary amine formed in the above neutralization was separated. The ether layer was washed with water and then dried. Evaporation of the ether in vacuo yielded as a residue 5.3 g. of a colorless oil comprising 3-(p-tolyloxy)-1-phenylpropylamine free base.

The other amine hydrochlorides produced in Example 1 are converted to the corresponding free base by the above procedure.

EXAMPLE 3

Preparation of N,N-Dimethyl 3-(p-Tolyloxy)-1-phenylpropylamine

Six milliliters of 90% formic acid were cooled to about 0° C. in an ice-water bath. 6.5 g. of 3-(p-tolyloxy)-1-phenylpropylamine were added thereto with stirring followed by the addition of 4 ml. of 37% aqueous formaldehyde. The mixture was stirred at ambient temperature for about 4 hours and was then heated at reflux temperature for about 3.5 hours. 2.3 ml. of 12 N aqueous hydrochloric acid were added and the volatile constituents removed by evaporation in vacuo. The residual oil, comprising N,N-dimethyl 3-(p-tolyloxy)-1-phenylpropylamine hydrochloride formed in the above reaction, was diluted with water and the aqueous mixture extracted with 200 ml. of ether. The acidic layer contained the desired tertiary amine was separated and then made basic with 5 N aqueous sodium hydroxide. The amine, being insoluble in base, separated and was thrice extracted with ether. The ether extracts thus obtained were combined and the combined extracts washed with water and then dried. Evaporation of the ether in vacuo yielded 6 g. of a pale yellowish oil comprising N,N-dimethyl 3-(p-tolyloxy)-1-phenylpropylamine.

The residual oil was dissolved in ether and anhydrous hydrochloric acid passed through the ether solution. N,N-dimethyl 3-(p-tolyloxy)-1-phenylpropylamine hydrochloride precipitated and was collected by filtration. Recrystallization from an ethylacetate-methanol solvent mixture yielded N,N-dimethyl 3-(p-tolyloxy)-1-phenylpropylamine hydrochloric melting at 181°–183° C.

Analysis calc.: C, 70.69; H, 7.91; N, 4.58; Cl, 11.59. Found: C, 70.67; H, 7.65; N, 4.71; Cl, 11.30.

Following the above procedure, 3-(p-anisyloxy)-1-phenylpropylamine hydrochloride from Example 1 was converted to the corresponding free base by the procedure of Example 2. The free base was methylated by the above procedure to yield N,N-dimethyl 3-(p-anisyloxy)-1-phenylpropylamine, purified as the hydrochloride salt melting at 141°–144° C.

Analysis calc: C, 67.17; H, 7.52; N, 4.35; Cl, 11.02. Found: C, 66.98; H, 7.41; N, 4.52; Cl, 11.11.

EXAMPLE 4

Preparation of N,N-Dimethyl 3-(o-Anisyloxy)-1-phenylpropylamine

A reaction mixture containing 98 g. of potassium hydroxide, 1.5 l. of methanol and 168 ml. of guaiacol was placed in a 3 l. 3-neck round-bottom flask equipped with mechanical stirrer, condenser and calcium sulfate drying tube. After stirring the reaction mixture for about 5 minutes, 199 g. of 3-phenylpropylbromide were added. The reaction mixture was heated to reflux temperature overnight and then cooled. The methanol was removed by evaporation in vacuo. The resulting residue was dissolved in ether and the ether solution washed once with water, twice with 5 N aqueous sodium hydroxide, twice more with water and finally with saturated aqueous sodium chloride. The ether layer was dried and the ether removed therefrom by evaporation in vacuo. The residue, comprising 1-phenyl-3-(o-anisyloxy)-propane formed in the above reaction, melted at 55°–57° C. after recrystallization from hexane; yield=195 g.

Analysis calc.: C, 79.31; H, 7.49. Found: C, 79.11; H, 7.28.

Using a similar procedure to that above, a reaction mixture was prepared containing 48 g. of N-bromosuccinimide, 65 g. of 1-phenyl-3-(o-anisyloxy)propane and 300 ml. of carbon tetrachloride. 500 mg. of benzoyl peroxide were added and the resulting mixture heated at reflux for about 2 hours at which point thin-layer chromatography indicated that no starting material remained in the reaction mixture. The reaction mixture was cooled, the succinimide separated by filtration and the solvent removed from the filtrate by evaporation in vacuo. A residual oil weighing about 88 g. comprising 1-phenyl-3-(o-anisyloxy)propylbromide formed in the above reaction was obtained.

The following quantities of material were placed in a stainless steel reaction vessel: 100 ml. of anhydrous dimethylamine, 200 ml. of anhydrous ethanol and 31 g. of 1-phenyl-3-(o-anisyloxy)propylbromide. The reaction vessel was sealed and heated to 140° C. for 16 hours, after which time the contents of the vessel were removed and the ethanol evaporated therefrom under reduced pressure. The residue, comprising N,N-dimethyl 3-(o-anisyloxy)-1-phenylpropylamine formed in the above reaction, was dissolved in 200 ml. of 2 N aqueous sulfuric acid. The acidic aqueous solution was extracted with 300 ml. of ether and the ether extract discarded. The acidic aqueous layer was made basic with 5 N aqueous sodium hydroxide and the resulting basic solution extracted three times with 20 ml. portions of ether. The ether extracts were combined and the combined extracts washed twice with water, and twice with saturated aqueous sodium chloride. The combined extracts were dried and the ether evaporated therefrom to yield a 20 g. residue of a dark oil comprising N,N-dimethyl 3-(o-anisyloxy)-1-phenylpropylamine. The compound was distilled and boiled in the range 161°–162° C. at 0.05–0.1 torr.; yield=12.3 g.

N,N-Dimethyl 3-(o-anisyloxy)-1-phenylpropylamine hydrochloride was prepared by dissolving the free base obtained above in ether and saturating the ethereal solution with anhydrous gaseous hydrogen chloride. The insoluble hydrochloride salt was collected by filtration. Recrystallization of the collected salt from an ethyl acetate-acetone solvent mixture yielded N,N-dimethyl 3-(o-anisyloxy)-1-phenylpropylamine hydrochloride melting at 159°–160.5° C.

Following the above procedure but using phenol in place of m-methoxyphenol, there was prepared 1-phenyl-3-phenoxypropane distilling at 146°–9° C. at 6 torr. This propane derivative was brominated α to the phenyl group with N-bromosuccinimide and benzoyl peroxide to yield 1-phenyl-3-phenoxypropylbromide which compound was in turn reacted with dimethylamine in a sealed reaction vessel to yield N,N-dimethyl 1-phenyl-3-phenoxypropylamine boiling in the range 116°–118° C. at 0.3 torr. The hydrochloride salt was prepared by the above procedure to yield N,N-dimethyl 1-phenyl-3-phenoxy-propylamine hydrochloride melting at 165°–167° C. after recrystallization from an ethyl acetate/acetone solvent mixture.

Analysis calc.: C, 69.97; H, 7.60, N, 4.80; Cl, 12.15. Found: C, 69.76; H, 7.38; N, 4.78; Cl, 12.25.

1-Phenyl-3-(p-trifluoromethylphenoxy)propane, prepared by the above procedure or by the procedure of Example 5 which follows was brominated α to the phenyl group to yield 1-phenyl-3-(p-trifluoromethylphenoxy)propylbromide. The bromide was a solid which melted at 61°–63° C. after recrystallization from ethanol.

Analysis calc.: C, 53.58; H, 3.93. Found: C, 53.50; H, 3.92.

Still following the above procedure, 1-phenyl-3-(p-trifluoromethylphenoxy)propylbromide was reacted with dimethylamine in a sealed vessel at 150° C. for a period of 8 hours. N,N-dimethyl 1-phenyl-3-(p-trifluoromethylphenoxy)-propylamine thus formed was converted to the hydrochloride salt by the addition to the reaction mixture of 100 ml. of 10% aqueous HCl. The hydrochloride salt was isolated therefrom and melted at 178°–180° C. after recrystallization from an ethyl acetate-hexane solvent mixture.

Analysis calc.: C, 60.08; H, 5.88; N, 3.89. Found: C, 59.80; H, 5.99; N, 4.08.

N-methyl 1-phenyl-3-(p-trifluoromethylphenoxy)-amine was prepared by reacting methylamine with 1-phenyl-3-(p-trifluoromethylphenoxy)propylbromide in a sealed vessel according to the above procedure. The compound was isolated as the hydrochloride salt which melted at 155°–156° C. after several recrystallizations from an ethyl acetate-hexane solvent mixture.

Analysis calc.: C, 59.05; H, 5.54; N, 4.05; Cl, 10.25. Found: C, 58.79; H, 5.41; N, 3.89; Cl, 10.02.

Following the above procedure but using methylamine in place of dimethylamine in the reaction with 1-phenyl-3-phenoxypropylbromide, there was prepared N-methyl 3-phenoxy-1-phenylpropylamine which was purified as the hydrochloride salt melting at 110°–113° C. after recrystallization from acetone.

Analysis calc.: C, 69.18; H, 7.26; N, 5.08; Cl, 12.76. Found: C, 69.18; H, 7.00; N, 5.03; Cl, 12.93.

Following the above procedure but substituting methylamine for dimethylamine in the reaction with 1-phenyl-3-(o-anisyloxy)propylbromide, there was prepared N-methyl 1-phenyl-3-(o-anisyloxy)propylamine which was purified as the hydrochloride salt melting at 147°–149° C. after recrystallization from an ethyl acetate-methanol solvent mixture.

Following the above procedure but substituting anhydrous ammonia for dimethylamine in the reaction with 1-phenyl-3-(o-anisyloxy)propylbromide in a closed vessel at 140° C., there was prepared 1-phenyl-3-(o-anisyloxy)propylamine which was purified and isolated as the hydrochloride salt melting at 171°–172° C.

Following the above procedure but substituting anhydrous ammonia for dimethyl or monomethylamine in the reaction with 1-phenyl-3-(p-trifluoromethylphenoxy)propylbromide, there was prepared 1-phenyl-3-(p-trifluoromethylphenoxy)propylamine which was isolated and purified as the hydrochloride salt melting at 222°–224° C.

Analysis calc.: C, 57.93; H, 5.17; N, 4.22. Found: C, 57.73; H, 5.16; N, 4.27.

1-Phenyl-3-phenoxypropylamine was prepared by the reaction of anhydrous ammonia and 1-phenyl-3-phenoxypropylbromide in a sealed vessel by the above procedure. The compound distilled at 137°–139° C. at 0.03 torr. The corresponding hydrochloride salt melted at 159°–161° C. after recrystallization from an ethyl acetate-acetone solvent mixture Analysis calc.: C, 68.30; H, 6.88; N, 5.31; Cl, 13.44. Found: C, 68.13; H, 6.65; N, 5.10; Cl, 13.46.

EXAMPLE 5

Alternate Preparation of 3-(p-Trifluoromethylphenoxy)-1-phenylpropane

Eight grams of sodium hydride were added slowly to a stirred mixture containing 72 g. of 1-phenyl-1-bromo-3-chloropropane and 50 g. of p-trifluoromethylphenol in 600 ml. of dimethylsulfoxide. The reaction temperature was maintained at about 30° C. with external cooling. After all the sodium hydride had been added, the reaction mixture was stirred overnight at room temperature and was then extracted with hexane. The hexane extract was separated, washed with water and dried. The hexane was removed by evaporation in vacuo. The residual oil distilled at about 110° C. at 1 torr. to give a mixture of 1-phenyl-1-(p-trifluoromethylphenoxy)-propylchloride and 1-phenyl-3-(p-trifluoromethylphenoxy)-1-propene (see Sliwa et al, Bull. Soc. Chem. France, 1972, 1540 for the production of a similar compound by the reaction of the sodium salt of phenol and 1-phenyl-1-bromo-3-acetoxypropane to yield 1-phenyl-3-phenoxy-1-propene). The distillate was dissolved in a 1:1 hexane/ethyl acetate solvent mixture and the solution cooled. 1-Phenyl-3-(p-trifluoromethylphenoxy)-1-propene solidified and was separated by filtration from the propylchloride product which was an oil. About a 50% yield of the propene compound was obtained. Recrystallization from acetonitrile yielded crystalline 1-phenyl-3-(p-trifluoromethylphenoxy)-1-propene melting at 92°–94° C.

Analysis calc.: C, 69.06; H, 4.71. Found: C, 69.35; H, 4.94.

A solution of 144 g. of the above 1-propene was dissolved in 40 ml. of anhydrous ethanol to which was added 14.5 g. of 5% palladium-on-carbon. The mixture was placed in a low pressure hydrogenation apparatus and hydrogenated at 50 psi until the theoretical quantity of hydrogen had been absorbed. The hydrogenation mixture was removed from the apparatus and the catalyst separated by filtration. The solvent was removed from the filtrate by evaporation and the residue comprising 1-phenyl-3-(p-trifluoromethylphenoxy)-propane formed in the above hydrogenation yielded, after recrystallization from methanol, crystals melting 45°–46° C.; total yield=114 g.

Analysis calc.: C, 68.56; H, 5.39. Found: C, 68.81; H, 5.17.

EXAMPLE 6

Preparation of Salts

Salts of the free bases of this invention, other than the hydrochloride, maleate and oxalate salts whose preparation is illustrated in Examples 1–5, are prepared by dissolving the free base in ether and adding an equivalent of a suitable non-toxic acid, also in ether. The salts thus formed, as for example the acetate and benzoate salts, are insoluble in ether and can be isolated by filtration. Alternatively, the amine base can be dissolved in ethanol and an equivalent of the acid added as an ethanolic solution. In this instance, since the salts thus formed are soluble in the reaction mixture, they are isolated by evaporation of the solvent in vacuo. Salts which can be formed by the above procedure include the sulfate, hydrobromide, phosphate, hydrogen phosphate, dihydrogen phosphate, acetate, methanesulfonate, succinate, tartrate, citrate, benzoate, and p-toluene sulfonate salts.

As indicative of their psychotropic activity, the compounds of this invention have been found to block the uptake of various physiologically active monoamines. This blockade is shown both in vitro using radioactive labelled compounds to determine the amount of monoamine uptake by synaptosomes from rat brain, and in vivo by a variety of methods using the procedure of Wong and Bymaster, *Biochem. Pharmacol.*, 25, 1978 (1976). Among the physiologically active monoamines whose uptake is blocked by the compounds of this invention are included serotonin, norepinephrine and dopamine (3,4-dihydroxyphenylethylamine). While all of the compounds of this invention block the uptake of monoamines, certain of them possess a unique selectivity in that they block the uptake of one monoamine to a far greater extent than they do the uptake of others. Table 1 which follows sets forth the results of some of the in vitro determinations of the blockage of monoamine uptake by the compounds of this invention. In the table, column 1 gives the R substituent on the 1-phenyl-propylamine, colums 2 and 3, the $R^1$ and $R^2$ substituents on the amine nitrogen and columns 3–4, the concentration in micrograms per ml. that blocks the uptake of a particular amine by 50 percent ($IC_{50}$) for the amines, serotonin and norephinephrine. At the head of each column is given the concentration of the particular monoamine used in the experiment.

Table 1

$$R-O-CH_2-CH_2-CH(C_6H_5)-NR^1R^2$$

| R | $R^1$ | $R^2$ | IC$_{50}$ Serotonin 0.1 μM | IC$_{50}$ Norepinephrine 0.48 μM |
|---|---|---|---|---|
| phenyl | H | H | 5.6 | 0.56 |
|  | CH$_3$ | H | 1.0 | 0.36 |
|  | CH$_3$ | CH$_3$ | 1.0 | 0.70 |
| p-trifluoromethyl phenyl | H | H | 0.32 | 10 (23%) |
|  | CH$_3$ | H | 0.21 | 10 (23%) |
|  | CH$_3$ | CH$_3$ | 0.21 | 10 (31%) |
| o-tolyl | H | H | 0.35 | 4.6 |
| m-tolyl | H | H | 1.4 | 5.7 |
|  | CH$_3$ | CH$_3$ | 0.08 | 5.1 |
| p-tolyl | H | H | 0.4 | 2.1 |
|  | CH$_3$ | CH$_3$ | 0.08 | 5.0 |
| o-anisyl | H | H | 4.3 | 1.4 |
|  | CH$_3$ | H | 0.5 | 0.5 |
|  | CH$_3$ | CH$_3$ | 0.1 | 0.3 |
| m-anisyl | H | H | 2 | 3 |
| p-anisyl | H | H | 0.35 | 7 |
|  | CH$_3$ | CH$_3$ | 0.28 | 5.1 |

One compound of this invention, N,N-dimethyl 3-(p-tolyloxy)-1-phenylpropylamine, is particularly active in inhibiting the uptake of biogenic amines. The uptake of serotonin in cortical synaptosomes and in platelets of human plasma in the presence of this compound were studied. Corticosynaptosomes were prepared as follows: Sprague-Dawley rats weighing about 150 g. were decapitated and their brains immediately removed and dissected. Crude synaptosomes were prepared from a 10 percent homogenate in 0.32 M scurose and in 10 μM glucose by differential centrifugation according to the procedure of Wong and Bymaster (loc. cit.). Procedures for measuring uptake of various radioactive amines were according to published methods including Wong and Bymaster (loc. cit.) and Wong, et al. *J. Pharmacol. Exp. Ther.*, 193, 804 (1975). The effect of N,N-dimethyl 3-(p-tolyloxy)-1-phenylpropylamine at 3 different concentrations (0.01, 0.05, and 0.1 μM) on the uptake of serotonin was examined and the results suggested that the compound competitively inhibited uptake of serotonin with an inhibitor constant K$_I$ =0.06 μM. In a similar experiment involving inhibition of norepinephrine uptake, it was again found that the same compound competitively inhibited the uptake of norepinephrine with an inhibitory constant K$_I$=2.2 μM.

The effect of N,N-dimethyl 3-(p-tolyloxy)-1-phenylpropylamine on uptake of dopamine from synaptosomes isolated from corpus striatum idicated that the compound inhibited the process of dopamine uptake against its substrate with an inhibitor constant K$_i$=2.5 μM.

A study of the uptake of serotonin from platelets was carried out as follows: platelet-rich plasma from human volunteers was prepared according to the method of Sneddon, *Brit. J. Pharmacol.*, 37, 680 (1969). The platelet uptake of serotonin was determined by the procedure of Horng and Wong, *Biochem. Pharmacol.*, 25, 865 (1976). It was determined that the compound blocked the uptake of serotonin by platelets with an estimated IC$_{50}$ value of 14 nanomoles (compared with 22 nanomoles for fluoxetine [(N-methyl 3-(p-trifluoromethylphenoxy)-3-phenylpropylamine].

The compounds of this invention have also been shown to be effective inhibitors of serotonin uptake in vivo. Using N,N-dimethyl 3-(p-tolyloxy)-1-phenylpropylamine as exemplary of those compounds, interperitoneal injection of the compound as the hydrochloride salt inhibited the uptake of serotonin by hypothalamic synaptosomes with a calculated ED$_{50}$ (effective dose) value of 12 mg/kg. There was also a decrease in norepinephrine uptake at a 100 mg./kg level but the reduction was less than 50% at this high dose level.

The tricyclic antidepressant drugs presently being marketed inhibit the uptake of monoamines by brain neurons, most of them being more effective in inhibiting the uptake of norepinephrine than of serotonin. Many of the compounds of this invention behave similarly in that they block norepinephrine uptake more effectively than they do serotonin uptake. On the other hand, some of the drugs, particularly N,N-dimethyl 3-(p-tolyloxy)-1-phenylpropylamine, are far more effective in inhibiting serotonin uptake than in inhibiting norepinephrine uptake. Thus, although these compounds clearly have potential as anti-depressant compounds in their ability to block monoamine uptake by brain neurons, it is apparent that cerain of the compounds will have a different type of anti-depressant action from the presently marketed drugs. The compounds of this invention may also find use in the treatment of schizophrenia according to the hypothesis of Wyatt et al., *Science*, 177 (1972) who were able to produce mild to moderate improvement in 6 of 7 chronic undifferentiated schizophrenic patients by the oral administration of l-5-hydroxytryptophane, a serotonin precursor.

In addition to their usefulness as psycotropic agents, the above compounds may also find use in treating disorders of sleep, sexual performance, appetite, muscular function, and pituitary function. All of these physiologic functions have been shown to be subject to influence by brain serotoninergic neural systems.

In treating humans suffering from various psychoses having a depressive component, the compounds of this invention can be given orally or parenterally. In either instance, it is preferred to use an acid addition salt of the compound formed with a pharmaceutically-acceptable non-toxic acid. For purposes of oral administration, the salt can be mixed with standard pharmaceutical excipients and placed in telescoping gelatin capsules. Similarly, the compound can be mixed with starch, binders, etc. and formulated into tablets, which tablets may be scored for ease of divided dosage administration. For parenteral administration, a water soluble salt of a compound of this invention, which salt is pharmaceutically-acceptable, is dissolved in an isotonic solution and administered intramuscularly, intravenously or subcutaneously. For chronic administration, the oral pharmaceutical forms are naturally preferred. The dose level should vary from 1 to 50 mg./dose given from 1 to 4 times a day with a total daily dosage of 1 to 200 mg./day/human.

We claim:

1. A compound of the formula:

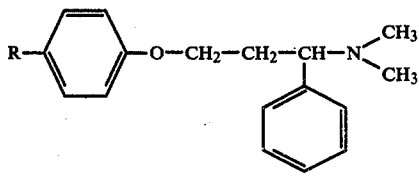

wherein R is CH₃ or CF₃ and pharmaceutically-acceptable acid addition salts thereof.

2. A compound according to claim 1, said compound being N,N-dimethyl-3-(p-tolyloxy)-1-phenylpropylamine.

3. A compound according to claim 1, said compound being N,N-dimethyl-3-(p-trifluoromethylphenyl)-1-phenylpropylamine.

4. A pharmaceutical composition in unit dosage form, useful as an antidepressant agent, consisting per dosage unit of a pharmaceutical carrier and an amount within the range 1–50 mg. of N,N-dimethyl-3-(p-tolyloxy)-1-phenylpropylamine.

* * * * *